United States Patent [19]

May

[11] Patent Number: 5,578,025
[45] Date of Patent: Nov. 26, 1996

[54] SANITARY NAPKIN HAVING STIFFENING SIDE STABILIZERS

[75] Inventor: Melisse N. May, Cincinnati, Ohio

[73] Assignee: The Procter & Gamble Company, Cincinnati, Ohio

[21] Appl. No.: 271,392

[22] Filed: Jul. 6, 1994

[51] Int. Cl.$^6$ ..................................................... A61F 13/15
[52] U.S. Cl. ...................... 604/385.1; 604/368; 604/374
[58] Field of Search ............................... 604/358, 385.1, 604/367, 368

[56] References Cited

U.S. PATENT DOCUMENTS

| | | | |
|---|---|---|---|
| 1,102,759 | 7/1914 | Keffer | 604/354 |
| 1,946,626 | 2/1934 | Jurgensen | 604/358 |
| 2,507,197 | 5/1950 | deMatzdorf | 604/375 |
| 2,939,461 | 6/1960 | Joa . | |
| 3,400,718 | 9/1968 | Saijo . | |
| 3,572,342 | 3/1971 | Lindquist . | |
| 3,769,979 | 11/1973 | Freney . | |
| 4,321,924 | 3/1982 | Ahr | 604/385.1 |
| 4,608,047 | 8/1986 | Mattingly | 604/387 |
| 4,657,539 | 4/1987 | Hasse | 604/385 A |
| 4,701,177 | 10/1987 | Ellis et al. | 604/385 A |
| 4,752,349 | 6/1983 | Gebel | 156/267 |
| 4,753,645 | 6/1988 | Johnson | 604/378 |
| 4,994,052 | 2/1991 | Kimura | 604/355 |
| 5,009,653 | 4/1991 | Osborn, III | 604/385.1 |
| 5,019,063 | 3/1991 | Marsan et al. | 604/385.1 |
| 5,019,066 | 5/1991 | Freeland et al. | 604/385.2 |
| 5,069,677 | 12/1991 | Sakurai et al. | 604/370 |

FOREIGN PATENT DOCUMENTS

| | | | |
|---|---|---|---|
| 0335253A1 | 10/1989 | European Pat. Off. . | |
| 0400694 | 12/1990 | European Pat. Off. | 604/358 |
| 0471114 | 2/1992 | European Pat. Off. | A61F 13/15 |
| 2222069 | 10/1974 | France . | |
| 61-187854 | 8/1986 | Japan | A61F 13/15 |
| 2233235 | 1/1991 | United Kingdom | 604/385.1 |
| WO90/14063 | 11/1990 | WIPO . | |
| WO93/01781 | 2/1993 | WIPO . | |

OTHER PUBLICATIONS

Lionel S. Marks, "Mechanical Engineers Handbook", 1916, pp. 379–380 1st edition.

*Primary Examiner*—John G. Weiss
*Assistant Examiner*—Dennis Ruhl
*Attorney, Agent, or Firm*—Steven W. Miller; E. Kelly Linman; Jacobus C. Rasser

[57] ABSTRACT

A unitary disposable absorbent article, particularly a catamenial pad or incontinent pad, having stabilizer members along the longitudinal side edges to enable the pad to assume a configuration conforming closely to the perineal area of the human body thereby more readily intercepting bodily discharges and providing a barrier to side soiling. The absorbent articles of the present invention comprise a central absorbent panel; a pair of side wall panels extending outwardly from and along the side borders of the central absorbent panel; and an axis of flexural bending joining each side wall panel to the central absorbent panel. The absorbent articles are constructed of a liquid pervious topsheet, a liquid impervious backsheet joined to the topsheet, an absorbent core positioned between the topsheet and the backsheet, side flaps extending outwardly from and along the side edges of the absorbent core, and stabilizer members joined in the side wall panels with the laterally innermost edge of the stabilizer member being disposed at or laterally inward from the side edge of the absorbent core. Thus, the stabilizer members increase the flexural stiffness of the side wall panels so that the flexural stiffness of each side wall panel is greater than the flexural stiffness of the central absorbent panel of the absorbent article. The lateral compression of the side wall panels is also greater than the lateral compression of the central absorbent panel to allow the central absorbent panel to buckle and bend upward to conform to the body. Preferably, the stabilizer members are joined to the wearer's surface of the topsheet to further provide a barrier to the lateral flow of liquids along the top surface of the absorbent article.

15 Claims, 2 Drawing Sheets

SANITARY NAPKIN HAVING STIFFENING SIDE STABILIZERS

FIELD OF THE INVENTION

The present invention relates to unitary disposable absorbent articles such as incontinent pads or catamenial pads designed to fit within the wearer's undergarment; and, more particularly, to such incontinent pads or catamenial pads having stabilizer members joined along the sides to reduce soiling and improve fit.

BACKGROUND OF THE INVENTION

Disposable absorbent articles are designed to contain body exudates and to keep such body exudates from soiling adjacent clothing and undergarments. Thus, numerous improvements have been directed towards providing better containment of such body exudates within the absorbent article and reducing the occurrence of soiling of garments worn over the absorbent article. Side soiling of garments is particularly a problem with catamenial pads. Side soiling is enhanced by a lack of body fit between the pad and the wearer. It is thus desirable that such absorbent articles conform as closely as possible to the body of the wearer. Such a body-conforming capability is believed to increase the effectiveness of the catamenial pad by reducing the possibility that menses will travel around the perimeter of the catamenial pads and leak, particularly at the sides.

There have been a number of recent efforts to provide catamenial pads with improved body-conforming characteristics in order to improve the leakage performance of these products. In particular, sanitary napkins have been developed which are relatively thin and flexible to better conform the sanitary napkin to the wearer. Commercially successful sanitary napkins of this type are described in U.S. Pat. No. 4,950,264, issued to Osborn, III, on Aug. 21, 1990 and U.S. Pat. No. 5,009,653 issued to Osborn III, on Apr. 23, 1991. While these ultrathin and flexible absorbent articles work quite well, there remains a need to improve the side soiling performance of these products and to further improve their fit characteristics.

Therefore, there is a need for an absorbent article with improved side soiling containment performance and body fit.

Thus, it is an object of the present invention to provide unitary disposable absorbent articles such as catamenial pads or incontinent pads with improved side soiling containment performance.

It is an additional object of the present invention to improve the fit of such absorbent articles during use such that their surface conforms better to the corresponding shape of the human body.

It is a further additional object of the present invention to provide catamenial pads that more readily intercept menses when discharged.

Another object of the present invention is to provide a reduction of lateral and longitudinal overflow, causing reduced soiling of garments.

These and other objects of the present invention will be more readily apparent when considered in reference to the following description and when taken in conjunction with the accompanying drawings.

SUMMARY OF THE INVENTION

The present invention provides a unitary disposable absorbent article, particularly a catamenial pad or incontinent pad, having stabilizer members along the longitudinal side edges to enable the pad to assume a configuration conforming closely to the perineal area of the human body thereby more readily intercepting bodily discharges and providing a barrier to side soiling. The absorbent articles of the present invention comprise a central absorbent panel; a pair of side wall panels extending outwardly from and along the side borders of the central absorbent panel; and an axis of flexural bending joining each side wall panel to the central absorbent panel. The absorbent articles are constructed of a liquid pervious topsheet, a liquid impervious backsheet joined to the topsheet, an absorbent core positioned between the topsheet and the backsheet, side flaps extending outwardly from and along the side edges of the absorbent core, and stabilizer members joined in the side wall panels with the laterally innermost edge of the stabilizer member being disposed at or laterally inward from the side edge of the absorbent core. Thus, the stabilizer members increase the flexural stiffness of the side wall panels so that the flexural stiffness of each side wall panel is greater than the flexural stiffness of the central absorbent panel of the absorbent article. The lateral compression of the side wall panels is also greater than the lateral compression of the central absorbent panel to allow the central absorbent panel to buckle and bend upward to conform to the body. Preferably, the stabilizer members are joined to the wearer's surface of the topsheet to further provide a barrier to the lateral flow of liquids along the top surface of the absorbent article.

In an alternative embodiment, the stabilizer member is joined to the wearer's surface of the topsheet laterally outward from the edges of the stabilizer member. The inner edge of the stabilizer member is preferably not joined to the topsheet so that the stabilizer member can flexurally bend at the point of attachment causing the inner edge of the stabilizer member to stand up and away from the topsheet and thereby create a trough to contain lateral flowing liquid.

In one embodiment, the central absorbent panel of the absorbent article has a flexural stiffness of less than about 500 grams, (preferably less than about 400 grams, more preferably 300 grams, most preferably 200 grams) such as in thin or ultrathin sanitary napkins. By having a relatively flexible central absorbent panel and relatively stiffer side wall panels on a thin catamenial or incontinent pad, significant improvements in body confomity are achieved as well as leakage improvements.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners or to other absorbent articles such as incontinent pads, and the like.

Figure 1:
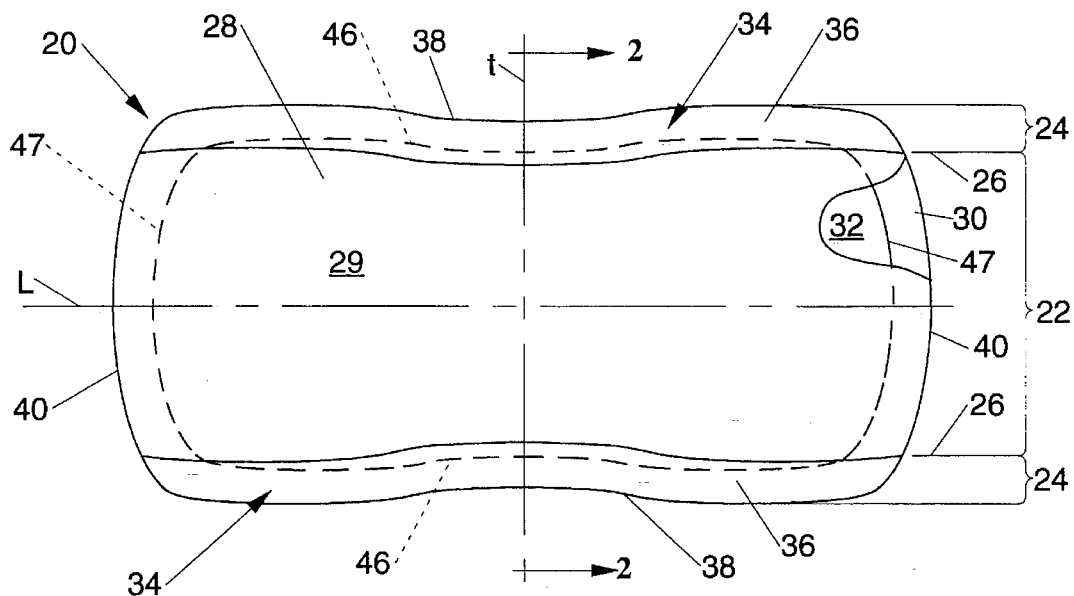
FIG. 1 is a top plan view of a preferred sanitary napkin of the present invention having stabilizer members.

FIG. 1 is a plan view of the sanitary napkin 20 of the present invention in its flat-out state with a portion of the structure being cut-away to more clearly show the construction of the sanitary napkin 20 and with the portion of the sanitary napkin 20 which faces the wearer, facing the viewer. As shown in FIG. 1, the sanitary napkin 20 comprises a central absorbent panel 22, a pair of side wall panels 24, and a pair of axes of flexural bending 26 flexurally joining the central absorbent panel 22 to the side wall panels 24. The sanitary napkin 20 is preferably constructed of a liquid pervious topsheet 28; a liquid impervious backsheet 30 joined with the topsheet 28; an absorbent core 32 positioned between the topsheet 28 and the backsheet 30; a side flap 34 extending outwardly from and along each side edge of the absorbent core 32; and stabilizer members 36. Each stabilizer member 36 is joined to the topsheet 28 in the side wall panel 24 of the sanitary napkin 20. In a preferred embodiment as shown in FIG. 1, the stabilizer member 36 is joined to the wearer's surface of the topsheet 28.

FIG. 1 shows a preferred embodiment of the sanitary napkin 20 in which the topsheet 28 and the backsheet 30 have length and width dimensions generally larger than those of the absorbent core 32. The topsheet 28 and the backsheet 30 extend beyond the edges of the absorbent core 32 to thereby form not only the side flaps 34 but also, preferably, portions of the periphery of the sanitary napkin. The periphery defines the outer perimeter or, in other words, the edges of the sanitary napkin. The periphery comprises the longitudinal edges 38 and the end edges 40. A particulary preferred construction for the sanitary napkin 20 is that described in U.S. Pat. Nos. 4,950,264 and 5,009,653 both entitled "Thin, Flexible Sanitary Napkin", issued to Osborn on Aug. 21, 1990 and Apr. 23, 1991, respectively. Both of these patents are incorporated herein by reference.

The sanitary napkin 20 has two centerlines, a principal longitudinal centerline "l" and a principal lateral or transverse centerline "t". The term "longitudinal", as used herein, refers to a line, axis or direction in the plane of the sanitary napkin 20 that is generally aligned with a vertical plane which bisects a standing wearer into left and right body halves when the sanitary napkin 20 is worn. This includes a line, axis or direction which is bent, curved or otherwise not strictly parallel to the vertical plane. The term "lateral" refers to the line, axis or direction generally perpendicular to the longitudinal direction and which lies within the plane of the sanitary napkin 20. The sanitary napkin 20 has a longitudinal dimension that runs in the general direction of the principal longitudinal centerline, l, and a lateral dimension that runs in the general direction of the principal lateral centerline, t. The sanitary napkin 20 is typically longer in the longitudinal dimension than in the lateral dimension.

The sanitary napkin 20 can be of any thickness (caliper), including relatively "thick" or relatively "thin". For the purposes of the present invention, a "thin" sanitary napkin will generally have a caliper in its central absorbent panel of less than or equal to about 7 mm, preferably less than or equal to about 5 mm, more preferably less than or equal to about 4 mm, and most preferably less than or equal to about 3 mm. A "thick" sanitary napkin will generally have a caliper in the central absorbent panel of greater than about 7 mm, preferrably greater than about 12 mm, more preferably greater than about 18 mm, and most preferably from about 18 mm to about 30 mm. The above calipers are to be measured with a comparator gauge having a test weight of 80.0 grams. The comparator gauge should have a comparator foot that weighs 10 grams and has a diameter of 2.54 centimeters. The comparator gauge should have a contact surface area of 5.06 square centimeters. The thickness of the side wall panels will typically be greater than the thickness of the central absorbent panel.

Figure 2:
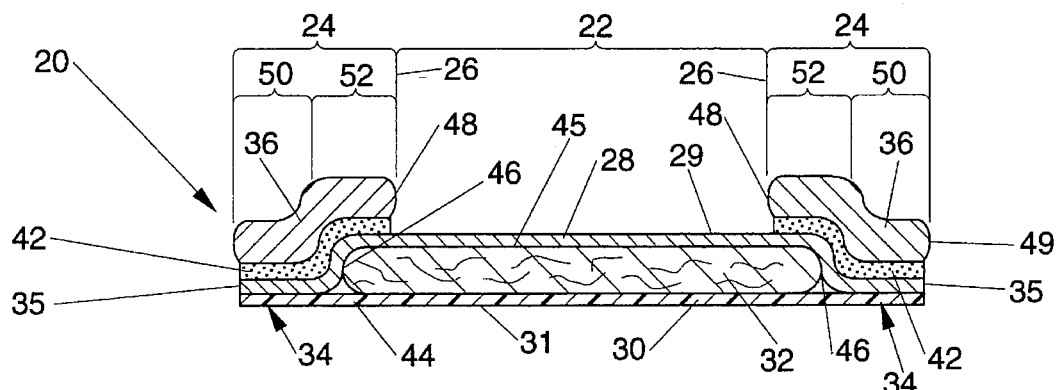
FIG. 2 is a cross-sectional view taken along line 2—2 of FIG. 1 showing the central absorbent panel and the side walls having the stabilizer members disposed therein.

FIG. 2 is a cross-sectional view of the sanitary napkin 20 taken along section line 2—2 of FIG. 1. FIG. 2 shows the central absorbent panel 22 which preferably comprises a portion of the absorbent core 32, the topsheet 28, and the backsheet 30; the side wall panels 24 which preferably comprise the stabilizer member 36, the side flap 34, and a portion of the topsheet 28, backsheet 30 and absorbent core 32; and the axes of flexural bending 26. The topsheet 28 and the backsheet 30 extend laterally across the entire cross-section to form each side flap 34. The absorbent core 32, which is generally depicted in FIG. 2, is positioned between the topsheet 28 and the backsheet 30 such that the topsheet 28 and the backsheet 30 encase the absorbent core 32. The stabilizer members 36 are joined to the wearer's surface 29 of the topsheet 28 by stabilizer attachment means such as the layer of adhesive 42 shown in FIG. 2. The stabilizer member 36 is laterally coextensive with the side flap 34 and extends laterally inward from the side edge 46 of the absorbent core 32. Thus, the side wall panels 24 of the sanitary napkin 20 include the stabilizer members 36, the side flaps 34, and a portion of the absorbent core/topsheet/backsheet configuration adjacent the side edge 46 of the absorbent core 32.

As shown in FIG. 2, the sanitary napkin 20 comprises a central absorbent panel 22, a pair of side wall panels 24, and a pair of axes of flexural bending 26. As used herein, the term "panel" is used to denote an area or element of the sanitary napkin. (For illustration purposes, the panels are delineated with brackets in FIG. 2.) The central absorbent panel 22 is that portion or region of the sanitary napkin 20 intended to absorb and contain the majority of the body exudates deposited onto the sanitary napkin. The central absorbent panel 22 thus comprises at least a portion of the absorbent core 32, and more preferably a portion of each of the topsheet 28, the backsheet 30, and the absorbent core 32. The side wall panels 24 are those portions extending outwardly from and along each of the side borders 56 of the central absorbent panel 22. The side wall panels 24 will form walls on the lateral sides of the sanitary napkin 20 when the sanitary napkin is compressed by the thighs of the wearer. As hereinafter discussed, the side wall panels 24 have a relatively significant flexural stiffness so that the side wall panels will not deform or compact in use and will maintain its shape to form walls during use. The side wall panels 24 thus comprise the stabilizer members 36 to increase the flexural stiffness of the side wall panels. Thus, the side wall panels 24 are generally defined by the zone where the laterally first edge 48 of the stabilizer member 36 is disposed (i.e., the size and shape of the central absorbent panel 22 will, therefore, ordinarily depend on the overall dimensions of the stabilizer members 36).

The flexural stiffness and lateral compression of the panels determines the resistance generally of the sanitary napkin to compression deformation and bending in each panel. In preferred embodiments of the present invention, the side wall panels have a substantial, predetermined, flexural stiffness and lateral compression to allow the side wall panels to resist compression and bending forces applied to it and to maintain the shape of the side wall panels during use.

The side wall panels have a flexural stiffness greater than the flexural stiffness of the central absorbent panel. Preferably the ratio of the flexural stiffness of the side wall panel to to the flexural stiffness of the central absorbent panel is at least about 1.25:1, preferably at least about 1.33:1, more preferably at least about 1.5:1. It has been found that the central absorbent panel has a flexural stiffness less than about 500 grams, preferably less than about 400 grams, more preferably less than about 300 grams, most preferably less than about 200 grams. The flexural stiffness of a panel can be determined using the method as hereinafter described.

The lateral compression of the side wall panels is greater than the lateral compression of the central absorbent panel. Thus, the force to compress the side wall panel to the same deflection as the central absorbent panel is greater than the force of the central absorbent panel. The lateral compression of the side wall panel at a given deflection is at least 1.25 times, preferably at least 1.5 times, more preferably at least 2.0 times, that of the central absorbent panel at at least one point on the force/deflection curve. The side wall panels 24 are flexurallly joined with the central absorbent panel 22 by an axis of flexural bending 26. As used herein, the term "flexurally joined" means a joint between panels adapted to allow relative flexural bending between the panel zones when forces are applied. An axis of flexural bending 26 can be constructed in various ways. Each axis of flexural bending preferably comprises a zone of structural discontinuity between panels. (i.e., the cross-sectional configuration of the panels may be varied to allow flexural bending between them.) For example, the materials making up the panels can be scored, compressed, embossed, creased, folded, bonded, reduced, cut, notched, slit, or eliminated to form an axis or axes of flexural bending. Typically, these methods will concentrate stresses/tensions to a particular line or axis through which flexural bending can occur. As shown in FIG. 2, each axis of flexural bending 26 preferably comprises the structural discontinuity formed by the absence of the stabilizer member 36 in the central absorbent panel 22. Thus, the axes of flexural bending 26 are created adjacent the first edge 48 of the stabilizer members 36, typically at the first edge 48. As an alternative, the axes of flexural bending may comprise a zone of material discontinuity between the panels (e.g., the material making up the panels may have a relative different modulus of bending or elasticity to provide an area or zone of different flexural resistance (differential flexural stiffness between the panels) which allows flexural bending between the panels.

The absorbent core 32 may be any absorbent means which is generally compressible, conformable, non-irritating to the wearer's skin, and capable of absorbing or retaining liquids such as vaginal fluids (e.g., menses) and other certain body exudates. As shown in FIGS. 1 and 2, the absorbent core 32 has a garment surface 44, a body surface 45, side edges 46 and pad edges 47.

The absorbent core 32 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding, meltblown polymers including coform, chemically modified or cross-linked cellulosic fibers, tissue including tissue wraps and tissue laminates, absorbent foams, absorbent sponges, peat moss, superabsorbent polymers, absorbent gelling materials, or any equivalent material or combinations of materials, or mixtures of these. The configuration and construction of the absorbent core may also be varied (e.g., the absorbent core may have varying caliper zones, hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinent pads, pantiliners, regular sanitary napkins, or overnight sanitary napkins.

An exemplary absorbent core for thick products is preferably a blend of comminuted wood pulp fibers, airfelt, and synthetic fibers such as polyester. This absorbent core is profiled in the lateral direction to be thicker in the central region of the absorbent core for improved absorbency and fit of the product. For pantiliners, the absorbent core preferably comprises one or more layers of tissue paper made in accordance with U.S. Pat. No. 4,191,609 issued to Trokhan on Mar. 4, 1980. Preferred absorbent structures for use as the absorbent core of "thin" sanitary napkins of the present invention that have achieved wide acceptance and commercial success are the superabsorbent tissue laminates described in the hereinbefore referenced U.S. Pat. Nos. 4,950,264 and 5,009,653 entitled "Thin, Flexible Sanitary Napkin" issued to Osborn III on Aug. 21, 1990 and Apr. 23, 1991, respectively. A preferred embodiment of the absorbent core has an hourglass shape such as shown in FIG. 1.

The backsheet 30 and the topsheet 28 are positioned adjacent the garment surface 44 and the body surface 45, respectively, of the absorbent core 32 and are preferably joined thereto and to each other by attachment means (not shown) such as those well known in the art. For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 30 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the sanitary napkin such as pants, pajamas and undergarments. The backsheet may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). An exemplary polyethylene film is manufactured by Clopay Corporation of Cincinnati, Ohio, under the designation Clopay 1401. The backsheet is preferably embossed and/or matte finished to provide a more clothlike appearance. Further, the backsheet may permit vapors to escape from the absorbent core while still preventing exudates and malodors from passing through the backsheet. The size of the backsheet is dictated by the size of the absorbent core and the exact sanitary napkin design selected. In a preferred embodiment, the backsheet extends beyond the absorbent core a minimum distance around the entire sanitary napkin periphery.

The topsheet 28 is compliant, soft feeling, and non-irritating to the wearer's skin. Further, the topsheet 28 is liquid pervious permitting liquids (e.g., menses and/or urine) to readily penetrate through its thickness. For the present invention, a preferred topsheet comprises an apertured plastic film. Apertured plastic films, more preferably formed films, are preferred for the topsheet because they are pervious to such body exudates and yet non-absorbent. Thus, the wearer's surface 29, the surface of the formed film which is in contact with the body, remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane and Smith on Apr. 13, 1982; U.S. Pat. No. 4,342,314 entitled "Resilient Plastic Web Exhibiting Fiber-Like Properties", which issued to Radel and Thompson on Aug. 3, 1982; and U.S. Pat. No. 4,463,045 entitled "Macroscopically Expanded Three-Dimensional Plastic Web Exhibiting Non-Glossy Visible Surface and Cloth-Like Tactile Impression", which issued to Ahr, Lewis, Mullane, and Ouellette on Jul. 31, 1984; each of which patents is incorporated herein by reference. The preferred topsheet for the present invention is the formed film described in one or more of the above patents and marketed by The Procter & Gamble Company of Cincinnati, Ohio as "DRI-WEAVE". Alternatively, the topsheet may be manufactured from a wide range of materials, such as porous foams; reticulated foams; or woven or nonwoven webs of natural fibers (e.g., wood or cotton fibers), synthetic fibers (e.g., polyester or polypropylene fibers), or a combination of natural and synthetic fibers.

In a preferred embodiment of the present invention, the wearer's surface 29 of the formed film topsheet is hydrophilic. The hydrophilic surface helps liquid to transfer through the topsheet faster than if the wearer's surface was not hydrophilic. This diminishes the likelihood that menstrual fluid will flow off the topsheet rather than being absorbed by the absorbent core. In a preferred embodiment, the wearer's surface of the topsheet is made hydrophilic by treating it with a surfactant. It is preferred that the surfactant be substantially evenly and completely distributed throughout the wearer's surface of the topsheet. This can be accomplished by any of the common techniques well-known to those skilled in the art. For example, the surfactant can be applied to the topsheet by spraying, by padding, or by use of transfer rolls. Further, the surfactant can be incorporated into the polymeric materials of the formed film topsheet.

A side flap 34 extends outwardly from and along each side edge 46 of the absorbent core 32. The side flaps 34 are that portion of the sanitary napkin 20 between the periphery and the side edges 46 of the absorbent core 32. In a preferred embodiment, the side flaps 34 are formed from the extension of the backsheet 30 and the topsheet 28 from and along the side edges 46 of the absorbent core 32. Each side flap 34 has a distal edge 35 which, in preferred embodiments, form the longitudinal edge 38 of the sanitary napkin 20.

The sanitary napkins of the present invention can also be provided with any optional additional components that are known in the art. Optional components may include one or several absorbent or fluid transport layers, secondary topsheets, optional interliners, fastening means, and a removable cover strip or release liner. The sanitary napkin may also be provided with flaps or "wings" (not shown in any of the drawings) that are folded around the crotch portion of the wearer's undergarment. Examples of such sanitary napkins are more fully described in U.S. Pat. No. 4,589,876 issued to Van Tilburg on May 20, 1986, and in U.S. Pat. No. 4,687,478 issued to Van Tilburg on Aug. 18, 1987, each of which is incorporated herein by reference.

In a preferred embodiment, the garment-facing surface of the backsheet 30 may include means for attaching the sanitary napkin 20 to the undergarment of the wearer, referred to hereinafter as pad attachment means (not shown in FIG. 1). Pad attachment means may include mechanical fasteners or, preferably, adhesive fastening means such as pressure-sensitive adhesive. A removable release liner preferably covers the adhesive fastening means in order to keep the adhesive from drying out or sticking to a surface prior to the usage of the sanitary napkin. The adhesive may be applied to the garment-facing surface of the backsheet in one, two or several parallel strips, or for example two symmetrically opposite convex outwardly oriented strips. The strips of adhesive may be between about 5 to about 35 mm, preferably between 15 mm and 26 mm, in width. Preferably the strips of adhesive are sized and disposed so that the distance between the inside edges of the strips is about 28 mm, and the distance between the outside edges of the strips is about 60 mm. Alternatively, the adhesive may be applied to the backsheet in a generally centered rectangular patch covering about 30% to about 70% of the area of the garment-facing surface of the backsheet. Suitable adhesive may be that specified as "0.6 mil pass" available from Century Adhesive as Product No. 8305-4 or from Anchor Continental, Inc., 3 Sigma Division of Covington, Ohio.

A stabilizing member 36 is disposed in each side wall panel 24 of the sanitary napkin 20 to increase the flexural stiffness of the side wall panels 24 beyond that of the central absorbent panel 22 so as to allow the sanitary napkin to configure itself into a shape that provides improved fit and allows better absorbent efficiency of the absorbent core 32. By stiffening the side wall panels 24 of the sanitary napkin 20, it is believed that the stabilizer members 36 allow the sanitary napkin to utilize the forces exerted onto the side wall panels 24 by the thighs of the wearer to configure the central absorbent panel 22, particularly the absorbent core 32 and the topsheet 28, closer and in more intimate contact with the pundendal area of the wearer. The improved contact of the central absorbent panel with the wearer reduces, in general, leakage from the sanitary napkin, and thus, the incidence of soiling. When disposed on and joined to the wearer's surface 29 of the topsheet 28, the stabilizer members 36 further improve lateral leakage performance by presenting a barrier wall against the lateral flow of body exudates.

Each stabilizer member 36 is preferably a separate element joined to the sanitary napkin 20 in the side wall panel 24. The term "stabilizer member" refers to an element which is a discrete, separate element joined to the sanitary napkin 20 in the side wall panel 24 to increase the flexural stiffness of the side wall panel 24. Thus, the stabilizer members 36 are preferably not formed from other elements of the sanitary napkin 20.

Figure 4:
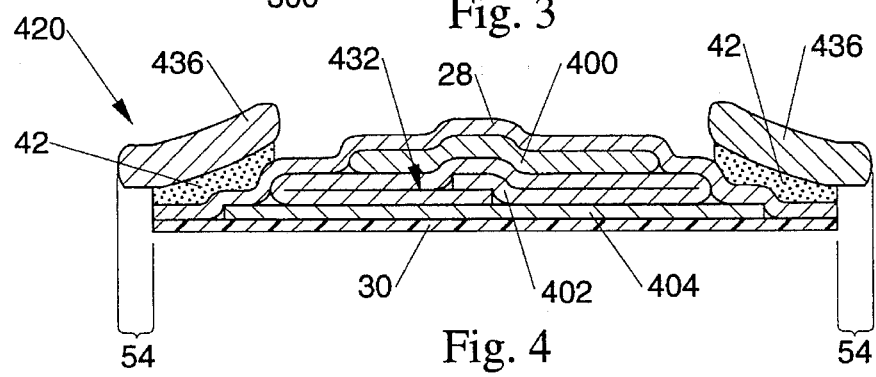
FIG. 4 is a cross-sectional view of another alternative embodiment of the present invention showing a further alternative attachment configuration and absorbent core for the sanitary napkin of the present invention.

Each stabilizer member 36 has a first edge 48, a second edge 49 laterally opposite the first edge 48, a side flap portion 50, preferably an inward core portion 50, and optionally an outward portion (not shown in FIGS. 1 or 2). The first edge 48 is the edge of the stabilizer member 36 extending in the longitudinal direction and that is closer to the longitudinal centerline, 1, of the sanitary napkin 20 than the second edge 49 (i.e., the second edge 49 is positioned laterally outward from the first edge 48). The first edge 48 and/or the second edge 49 of the stabilizer member 36 may be linear or arcuate. The first edge 48 of the stabilizer member 36 is disposed adjacent to or laterally inward from the side edge 46 of the absorbent core 32. The side flap portion 50 of the stabilizer member 36 extends from the side edge 46 of the absorbent core 32 toward and preferably to the distal edge 35 of the side flap 34. The stabilizer member 36 must be disposed in at least a portion of the side flap 34, preferably adjacent the side edges 46 of the absorbent core 32, to provide the increased flexural stiffness to the side wall panels 24 of the sanitary napkin 20. Preferably, the stabilizer member 36 also preferably comprises an inward core portion 50 contiguous with the side flap portion 50. The inward core portion 50 extends from the side edge 46 of the absorbent core 32 inward generally toward the longitudinal centerline, 1, to the first edge 48. Further, the stabilizer member 36 may optionally comprise an outward portion which extends outwardly beyond the distal edge 35 of the side flap 34 to the second edge 49 to form a soft, comfortable longitudinal edge for the sanitary napkin. (Such an embodiment is shown in FIG. 4.)

The stabilizer member 36 may be disposed anywhere through the thickness of the sanitary napkin 20 including on the wearer's surface 29 of the topsheet 28, between the absorbent core 32 and the topsheet 28, between the absorbent core 32 and the backsheet 30, or on the garment surface 31 of the backsheet 30. As shown in FIGS. 1 and 2, the stabilizer member 36 is preferably disposed on and joined to the wearer's surface 29 of the topsheet 28. As used herein, the term "joined" includes configurations whereby the stabilizer members are directly affixed to portions of the sanitary napkin and configurations whereby the stabilizer member is indirectly affixed to an intermediate member or members which are in turn affixed to the sanitary napkin. In a preferred embodiment, the stabilizer members are each directly joined to the topsheet 28 on the wearer's surface 29 by stabilizer attachment means, preferably such as the layer of adhesive 42 shown in FIG. 2.

The stabilizer members 36 may be joined to the topsheet 28 at a number of different locations, zones, and patterns. For example, the stabilizer member may be joined to the topsheet at a point (an attachment point) inward from the first edge so that the first edge may be spaced away from the wearer's surface of the topsheet during use to form a stand-up barrier to the lateral flow of body exudates. (This configuration is discussed in alternative embodiments of the present invention.) The stabilizer member need only be joined to the topsheet at two points. In one embodiment, only the edges of the stabilizer members may be secured to the topsheet such that area between the edges is not joined to the topsheet. In a preferred embodiment, the stabilizer members are joined to the topsheet along its entire length and width.

The stabilizer members 36 may have any surface area shape or cross-sectional shape which can provide the necessary stiffness as described herein. The surface area shape of the stabilizer member can be rectangular, trapezoidal, elliptical or any other surface area shapes. In general, the cross-sectional shape of the stabilizer member will depend on performance considerations like comfort and discreteness of the sanitary napkin for the wearer as well as manufacturing capability and packaging compatibility considerations of the producer of the sanitary napkin. According to the present invention, the cross-sectional shape of the stabilizer member can be of any shape such as a rectangular shape, an oval shape, round, or of a symmetrical or unsymmetrical (e.g., dog bone) type of shape. Particularly preferred are rectangular shapes which are rounded on all or some edges.

The stabilizer member 36 follows the underlying sanitary napkin 20 in its surface contour. This results in the execution shapes shown in FIGS. 2, 3, 5, and 6 showing a step-like appearance. However, the dimensions of the different materials shown in the drawings has been enlarged in order to provide clarity of the drawings. Therefore, the stabilizer member in practical executions will only display either a minor amount or no bending when following the contour of the underlying sanitary napkin 20.

The length (longitudinal dimension) of the stabilizer member 36 may vary depending upon the width, thickness, and cost of the material that forms the stabilizer members. The length of the stabilizer members will typically be as long as the absorbent core, generally as long as the sanitary napkin itself.

The stabilizer attachment means may be any attachment means as are known in the art for attaching the stabilizer member to the sanitary napkin in the side wall panels. For example, the stabilizer attachment means may comprise adhesives, heat/pressure seals using heat/pressure sealing techniques as are known in the art, ultrasonic bonds using ultrasonic bonding techniques as are known in the art, dynamic mechanical bonds using dynamic mechanical bonding techniques as are known in the art, or any other materials or methods as are known in the art. The panel attachment means are preferably an adhesive such as an adhesive layer 42 such as is shown in FIG. 2.

The stabilizer members 36 may be formed from a variety of materials which provide the function described herein. The material of the stabilizer member of the present invention is preferably soft feeling and non-irritating to the skin of the wearer. The material can be a homogeneous single material, a homogeneous mixture of different materials, or a non-homogeneous combination of different materials (e.g., a layered construction). In a preferred embodiment, the stabilizer member comprises a central homogeneous material fully wrapped in a wrapping web for cover layer. The stabilizer member materials can be, for example, the same as the absorbent core materials, the topsheet materials, or the backsheet materials as discussed above. The stabilizer member material will normally be a lofted, that is soft and thick, preferably resilient material, such as the airthrough bonded hydrophobic nonwoven with a basis weight of 60 grams as supplied by The Veratec Company of Walpole, Mass.

The material may also, for example, be selected to have an absorbent capacity or may be without absorbent capacity. If the stabilizer member has an absorbent capacity, the material chosen for the stabilizer member is preferably wet resilient so that it does not collapse when wetted. Suitable wet resilient materials include polyesters, rayons, orlons or other polyolefin materials. In a preferred execution, the stabilizer member is constructed from an absorbent, wet resilient material and wrapped in a cover layer of a web web of nonwoven or formed film material as described herein above for the topsheet materials.

The function provided by the stabilizer members 36 of the present invention is essentially to stiffen the side wall panels 24 so as to allow the sanitary napkin 20 to configure itself into a shape that allows better absorbent efficiency of the absorbent core 32 by dynamically moving the absorbent core 32 together with the topsheet 28 closer into the perineal area of the wearer. To perform this function, the sanitary napkin 20 is provided with stabilizer members 36 which stiffen the side wall panels 24 of the sanitary napkin 20 and thereby allow the sanitary napkin 20 to utilize the forces usually exerted onto the sides of the sanitary napkin 20 by the thighs of the wearer. Without wishing to be bound by any theory, it is believed that when the wearer brings her thighs together, compressive forces are exerted on the longitudnal sides of the sanitary napkin causing the side to be forced inwards. This inward movement of the sides consequently causes the side wall panels to bend about the axis of flexural bending and thereby assume a substantially vertical position. As the sanitary napkin is further compressed, the now substantially vertically standing walls formed by the side wall panels are displaced inward toward the central absorbent panel. The stiffened side wall panels thus compress inwards causing the central absorbent panel, which has less flexural stiffness than the side wall panels, to flex and move upward wherein the body surface of the sanitary napkin may make intimate contact with the external surfaces of the pundendal region, thereby causing better body contact. The stiffened side wall panels further provide vertically standing walls which provides an area where menses may collect until it is absorbed. Still further, the relatively thick stabilizer members provide a wall to block the lateral flow of exudates to the sides of the sanitary napkin.

The sanitary napkin is preferably placed in the crotch portion of the wearer's panty and secured thereto by the adhesive fastening means (not shown) after the release cover (not shown has been removed.

Figure 3:
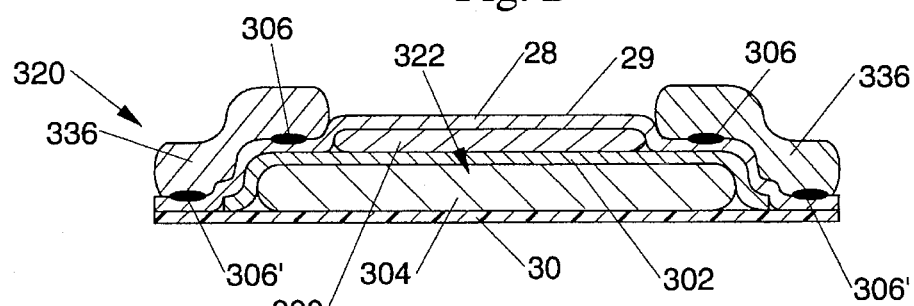
FIG. 3 is a cross-sectional view of an alternative embodiment of the present invention showing an alternative attachment configuration and absorbent core for the sanitary napkin of the present invention.

FIG. 3 is a cross-sectional view of an alternative embodiment of the sanitary napkin 320 of the present invention. The absorbent core 332 of the sanitary napkin 320 comprises a three layer structure comprising: an acquisition layer 300; a tissue layer 302; and a storage layer 304. The acquisition layer 300 is positioned adjacent the topsheet 28 to rapidly acquire and distribute menses or other body fluids. (Examples of suitable acquisition layers are described in U.S. Pat. No. 5,137,537 issued to Heran & Cooper on Aug. 11, 1992; U.S. Pat. No. 5,009,653 issued to Osborn III on Apr. 23, 1991; or WO 93/11725, The Procter & Gamble Company, published on Jun. 24, 1993; each of which is incorporated herein by reference. The tissue layer 302 is positioned between the acquisition layer 300 and the storage layer 304 in order to better distribute menses to the storage layer from the acquisition layer. (The tissue layer is preferably a layer of cellulose tissue such as is marketed by The Procter & Gamble Company under the trademark PUFFS or any other tissue as is known in the art.) The storage layer 304 is designed to retain menses and other body fluids. Thus, the storage layer 304 is positioned adjacent the backsheet 30, between the backsheet 30 and the tissue layer 302. (The storage layer can be any of the absorbent layers as described herein with respect to an absorbent core but is preferably the superabsorbent laminate such as is described in the above-referenced U.S. Pat. No. 4,950,264 and U.S. Pat. No. 5,009,653 of Osborn III.)

In the embodiment shown in FIG. 3, the stabilizer member 336 is joined to the sanitary napkin 320 at at least two discrete attachment points 306 and 306'. This allows portions of the stabilizer member 336 to float and be spaced away from adjacent portions of wearer's surface 29 of the topsheet 28. This is especially important at the first edge 48 of the stabilizer member 336 wherein it is preferred that the first edge 48 is not secured to the topsheet 28 so that the first edge 48 may be spaced away from the topsheet 28 during use to create a channel that contains menses that has flowed along the wearer's surface 29 of the topsheet 28. The attachment points 306 and 306' each preferably comprise an adhesive element joining the stabilizer member 336 to the topsheet 28.

FIG. 4 shows a further alternative embodiment of a sanitary napkin 420 of the present invention. The absorbent core 432 of the sanitary napkin 420 comprises a three layer structure comprising: a wipe acquisition layer 400; a C-folded superabsorbent laminate 402; and a tissue layer 404. The stabilizer member 436 is joined to the side flap 34 and extends laterally outwardly from the distal edge 35 of the side flap 34. The portion of the stabilizer member that extends laterally outwardly beyond the distal edge 35 of the side flap 34 is designated the outward portion 54 of the stabilizer member. The outward portion 54 forms a portion of the longitudinal edge 38 of the sanitary napkin 420 and creates a soft and compliant side for the sanitary napkin.

Figure 5:
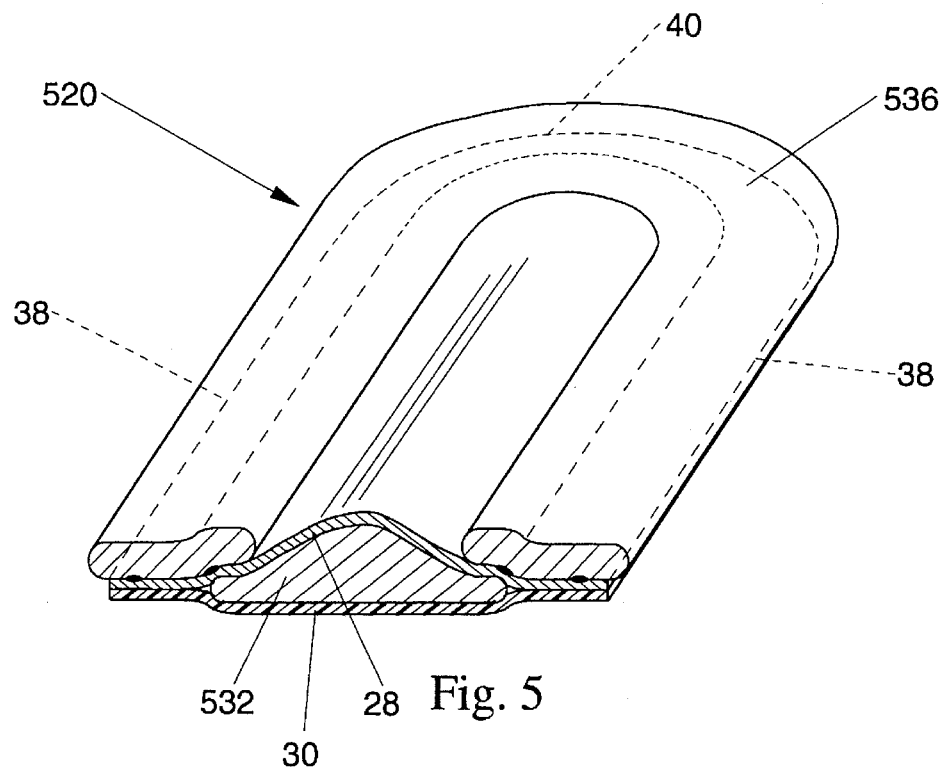
FIG. 5 is a perspective sectional view of an alternative embodiment of a stabilizer member joined to the wearer's side of a sanitary napkin and forming a closed line.

FIG. 5 shows a still further alternative embodiment of a sanitary napkin 520 of the present invention wherein the stabilizer member 536 is disposed continuously about the entire periphery of the sanitary napkin. Thus, the end edges 40 of the sanitary napkin 520 as well as the side wall panels 24 are stiffened to provide the benefits described herein. In the embodiment shown, the stabilizer member 536 preferably is formed from a single piece of material extending around the periphery of the sanitary napkin. Further, the absorbent core 532 of this embodiment has a profiled cross-section so that the center of the absorbent core is thicker than the lateral sides of the absorbent core.

Figure 6:
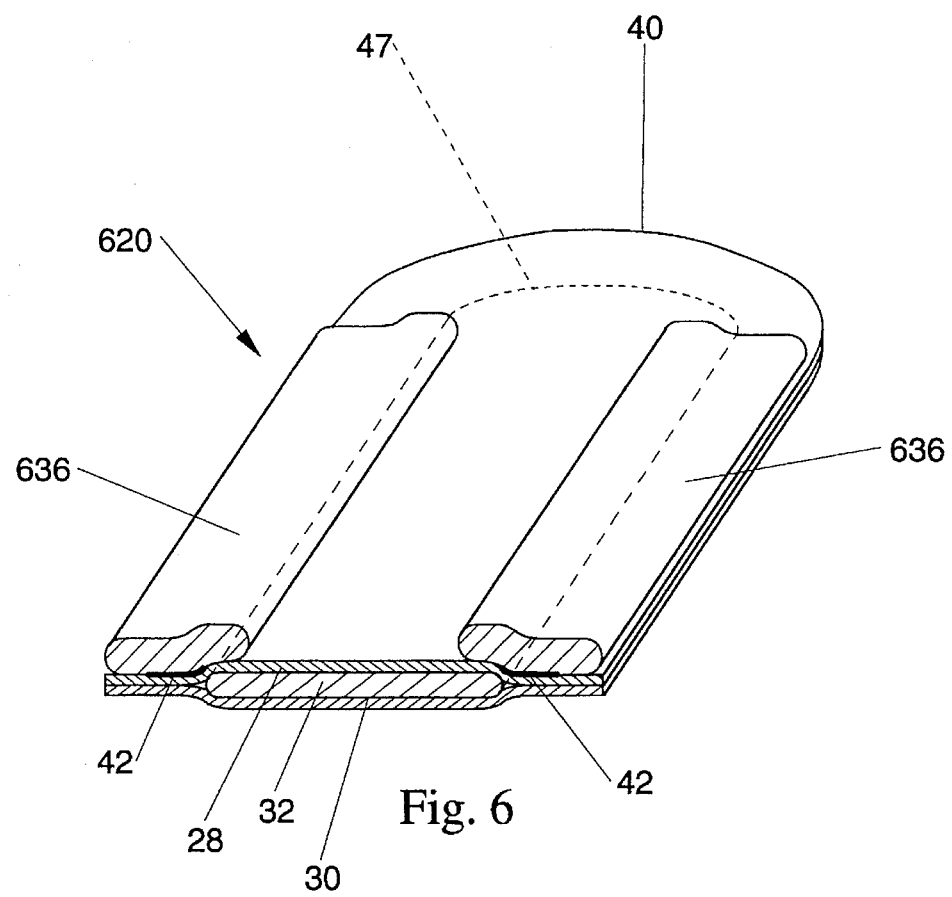
FIG. 6 is a perspective sectional view of a further alternative embodiment of a stabilizer member configuration of the present invention.

FIG. 6 shows a further alternative embodiment of a sanitary napkin 620 of the present invention wherein the stabilizer members 636 do not extend longitudinally to the end edges 40 of the sanitary napkin 620. The stabilizer members 636 preferably stop short of the pad edges 47 of the absorbent core 32 as well to stiffen only a central zone of the sanitary napkin.

TEST PROCEDURE

Flexural Stiffness

The flexural stiffness of the central absorbent panel and the side wall panels is determined its flexure resistance which is measured by peak bending stiffness. Peak bending stiffness is determined according to the Circular Bend Procedure test procedure set forth in U.S. Pat. No. 5,009,653 issued to Osborn III on Apr. 23, 1991; which patent is incorporated herein by reference. the peak bending stiffness for each specimen is the maximum force reading for that specimen.

Lateral Compression

The lateral compression of the samples is determined as follows:

A "constant rate of elongation" Tensile/Compression Tester such as the EME model 599A and computer as is available from EME, Inc of Newbury, Ohio is used with a load cell with a sensitivity of at least 5 grams and the ability to measure forces up to 2000 grams. The load cell should be calibrated so that force measurement are accurate to within 2% or better for forces above 100 grams. The tester's measurement of position should be accurate to at least 0.05 cm. The procedure is carried out in a room conditioned to 73 F.±2 F. with a relative humidity of 50±2% is used. Sample fixtures consist of two parallel circular plates 1.50 inches in diameter. One of the plates is clamped into the load cell clamp (stationary) and the other plate is affixed to the moving crosshead.

The sample to be tested is cut from the appropriate panel so as to have a size of 20 mm wide (lateral direction) by 38 mm long (longitudinal direction). The parallel plates are initially 3.75 cm apart. The plates are set to move together at a rate of 0.16 cm per second. The plates are set to move together until the computer detects a 2000 gram load, the n the crosshead return to its original position. The computer is set to acquire force and distance data at a rate of 40 points per second.

After loading the appropriate data acquisition file from the computer to the tensile tester, the conditioned sample is oriented with the 20 mm edge oriented vertically between the parallel plates in the tensile/compression tester. The sample is held in this orientation without applying force to the load cell. The start button is pushed to start the test sequence. The sample is held in place vertically until both plates just contact it whereupon the sample is released and allowed to compress freely. From the graph of the force and distance data, the maximum separation of the forces at a given deflection is determined which provides the lateral compression of the panels.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the invention.

What is claimed is:

1. An absorbent catamenial or incontinent pad comprising:
   (a) a liquid pervious topsheet having a wearer-facing side;
   (b) a liquid impervious backsheet joined with said topsheet;
   (c) an absorbent core positioned between said topsheet and said backsheet, said absorbent core having side edges;
   (d) a side flap extending laterally outwardly from and along each said side edge of said absorbent core, said side flap having a distal edge; and
   (e) a stabilizer member joined to at least each of said side flaps, each said stabilizer member having a first edge and a second edge laterally outwardly from said first edge, said first edge being disposed at or laterally inward from said side edge of said absorbent core, said stabilizer member being joined to said wearer-surface of said topsheet at at least two points of attachment, wherein the laterally inward most one of said points of attachment is positioned laterally outward from said first edge of said stabilizer member such that said first edge is not joined to said topsheet;

wherein the absorbent pad has a central absorbent panel having a flexure-resistance, said central absorbent panel having side borders defined by said first edge of each said stabilizer member;

a side wall panel extending outwardly from and along each said side border of said central absorbent panel, each said side wall panel being flexurally joined with said central absorbent panel, each said side wall panel having a flexure-resistance, each said side wall panel comprising said stabilizer member, said stabilizer member increasing the flexure-resistance of said side wall panel such that the flexure-resistance of each said side wall panel is greater than the flexure-resistance of said central absorbent panel; and an axis of flexural bending joining each said side wall panel to said central absorbent panel, each said axis of flexural bending being formed by the structural discontinuity formed by said stabilizer member.

2. The absorbent pad of claim 1 wherein said second edge of said stabilizer member extends laterally outwardly to at least said distal edge of said side flap.

3. The absorbent pad of claim 2 wherein said second edge extends laterally outwardly from said distal edge of said side flap.

4. The absorbent pad of claim 1 wherein said central absorbent pad has a thickness of less than about 7 mm.

5. The absorbent pad of claim 4 wherein said flexure-resistance of said central absorbent pad is less than about 400 grams.

6. The absorbent pad of claim 5 wherein said absorbent core comprises a tissue laminate comprising an absorbent layer and absorbent gelling material joined with said absorbent layer.

7. The absorbent pad of claim 1 wherein said stabilizer members each have a thickness of between about 1 mm and about 20 mm.

8. The absorbent pad of claim 7 wherein each said stabilizer member comprises a central member and a cover layer enclosing said central member.

9. The absorbent pad of claim 8 wherein said cover layer comprises a nonwoven material.

10. The absorbent pad of claim 8 wherein said cover layer comprises an apertured film.

11. An absorbent catamenial or incontinent pad comprising:

(a) a liquid pervious topsheet having a wearer-facing side;

(b) a liquid impervious backsheet joined with said topsheet;

(c) an absorbent core positioned between said topsheet and said backsheet, said absorbent core having side edges, said absorbent core comprising a tissue laminate comprising an absorbent layer and an absorbent gelling material joined with said absorbent layer;

(d) a side flap extending laterally outwardly from and along each said side edge from said absorbent core, said side flap having a distal edge; and (e) a stabilizer member joined to at least each of said side flaps, each said stabilizer member having a first edge and a second edge laterally outwardly from said first edge, said first edge being disposed at or laterally inward from said side edge of said absorbent core;

wherein the absorbent pad has a central absorbent panel having a flexure-resistance, said central absorbent panel having side borders defined by said first edge of each said stabilizer member, wherein said central absorbent panel has a thickness of less than about 7 mm and wherein said flexure-resistance of said central absorbent panel is less than about 400 grams;

a side wall panel extending outwardly from and along each said side border of said central absorbent panel, each said side wall panel being flexurally joined with said central absorbent panel, each said side wall panel having a flexure-resistance, each said side wall panel comprising said stabilizer member, said stabilizer member increasing the flexure-resistance of said side wall panel such that the flexure-resistance of each said side wall panel is greater than the flexure-resistance of said central absorbent panel; and an axis of flexural bending joining each said side wall panel to said central absorbent panel, each said axis of flexural bending being formed by the structural discontinuity formed by said stabilizer member.

12. The absorbent pad of claim 11 wherein said stabilizer members each have a thickness of between about 1 mm and about 20 mm.

13. The absorbent pad of claim 12 wherein each said stabilizer member comprises a central member and a cover layer enclosing said central member.

14. The absorbent pad of claim 13 wherein said cover layer comprises a nonwoven material.

15. The absorbent pad of claim 13 wherein said cover layer comprises an apertured film.

* * * * *